United States Patent [19]

Käsbauer et al.

[11] Patent Number: 4,782,190
[45] Date of Patent: Nov. 1, 1988

[54] PROCESS FOR THE PREPARATION OF 4-NITROPHENETOL

[75] Inventors: Josef Käsbauer; Karlfried Wedemeyer, both of Cologne, Fed. Rep. of Germany

[73] Assignee: Bayer Aktiengesellschaft, Leverkusen, Fed. Rep. of Germany

[21] Appl. No.: 22,834

[22] Filed: Mar. 6, 1987

[30] Foreign Application Priority Data

Mar. 29, 1986 [DE] Fed. Rep. of Germany ....... 3610707

[51] Int. Cl.$^4$ .................. C07C 79/35; C07C 41/16
[52] U.S. Cl. .................................................... 568/584
[58] Field of Search ......................................... 568/584

[56] References Cited

U.S. PATENT DOCUMENTS 1,619,368  3/1927  Pratt et al. .
2,166,917  7/1939  McCormack et al. .
3,085,113  4/1963  Knowles et al. ................... 568/584
4,454,355  6/1984  Schubert et al. .................... 568/584
4,479,015  10/1984 Sasson et al. ....................... 568/584

FOREIGN PATENT DOCUMENTS 81113    4/1971  German Democratic Rep. ..................... 568/584
626866  12/1981  Switzerland .

Primary Examiner—John F. Terapane
Assistant Examiner—Susan Wolffe
Attorney, Agent, or Firm—Sprung Horn Kramer & Woods

[57] ABSTRACT

4-Nitrophenetol is prepared by reaction of 4-chloronitrobenzene with ethanol and alkali metal hydroxides in the presence of phase-transfer catalysts by carrying out the reaction at temperatures from 60° to 95° C. and under pressure in the presence of oxygen-containing gases diluted with inert gases, there being at the start of the reaction 0.2 to 1.0 mol of alkali metal hydroxide metered each hour into the reaction mixture for each 1 mol of 4-chloronitrobenzene.

14 Claims, No Drawings

PROCESS FOR THE PREPARATION OF 4-NITROPHENETOL

BACKGROUND OF THE INVENTION

FIELD OF THE INVENTION

The invention relates to a process for the preparation of 4-nitrophenetol which is virtually free of 4-nitrophenol and 4,4'-dichloroazoxybenzene.

BACKGROUND OF INFORMATION

It is known to prepare 4-nitrophenetol by reaction of 4-chloronitrobenzene with alkali metal hydroxides and ethanol (C. Willgerodt, Chem. Ber., 15 (1882), 1002). The disadvantages of this preparation process are the low rate of reaction and the formation of azoxy compounds by reductive dimerization of the 4-nitrophenetol, and especially of the 4-chloronitrobenzene.

In order to suppress the formation of azoxy compounds attempts have been made to carry out the reaction in the presence of air or other oxidizing agents (see, for example, U.S. Pat. No. 2,545,597; GDR Patent Specification No. 81,113, Indian Chem. Mfr. 9(3), 21 to 22 (1971), Khim.-Farm. Zh., 8(6), 29 to 30 (1974), Yakhak Hoe Chi, 19(2), 101 to 110 (1975), Khim. Ind. (Sofia), 10, 451 to 453 (1981), Japan Kokai JP 49/126634 (1974) and J. Org. Chem., 45 (11), 2263 to 2264 (1980)).

The processes in the said publications have the disadvantage that they either provide an inadequate yield with a very long reaction time (JP 49/126634: 33 hours reaction time, 88.2% yield) or still form azoxy products with a short reaction time (for example, Khim. Ind. (Sofia) 10, 451 to 453 (1981): 7 hours, 0.6% 4,4'-dichloroazoxybenzene, up to 90% yield) or that there is still formation of 4-nitrophenol with a long reaction time (for example U.S. Pat. No. 2,545,597: 24 hours, 5% nitrophenol). The nitrophenol which is formed is a nuisance both in the further processing of 4-nitrophenetol, as well as owing to its solubility in water.

It is furthermore known to carry out the reaction of 4-chloronitrobenzene with alkali metal hydroxides and ethanol to give 4-nitrophenetol even without the addition of oxidizing agents. Thus, in DE-OS (German Published Specification No.) 2,634,419, there is a description of a process for the preparation of aromatic ethers which is characterized in that an acetylated aromatic halide which is immiscible with water and in which the halogen atom comprises a nuclear substituent is reacted with an organic hydroxy compound in the presence of an aqueous alkali and of a phase-transfer catalyst. According to Example 6 of the DE-OS 2,634,419, under reflux conditions, while the yield of 4-nitrophenetol is 90%, there is still 10% of 4,4'-dichloroazoxybenzene obtained. The occurrence of this by-product impedes the working up of the 4-nitrophenetol and is a nuisance in the further reaction of 4-nitrophenetol.

In European Patent Application No. 65,770 there is a description of the preparation of p-nitrophenetol from pchloronitrobenzene and ethanol by heating with the addition of alkali metal hydroxides and phase-transfer catalysts, the reaction being carried out at temperatures from 60° to 80° C. According to Example 1 of European Patent Application No. 65,770 at a temperature of 70° C. 4-nitrophenetol is obtained in 94.8% yield. The disadvantages of this process are the large required amounts of phase-transfer catalyst, at 8.5% by weight, and the narrow limits on temperature control. Thus, it is shown in the comparison example that, under reflux conditions, there is formation of 13% of 4,4'-dichloroazoxybenzene and 10% of 4,4'-diethoxyazoxybenzene in addition to 2% of 4-nitrophenol. In Example 2 of European Patent Application No. 65,770, the importance of strict temperature control is emphasized once more, since it is expressly pointed out that during the entire reaction time the reaction temperature must not rise above 70° C.

Care is also taken about strict temperature control in the process according to DE-OS (German Published Specification No.) 3,307,164. In the final paragraph on page 9 in DE-OS 3,307,164 it is in fact emphasized for the process for the preparation of o- or p-nitrophenetol that some azoxy compounds start to be formed at temperatures above 80° C., for which reason it is said to be extremely advantageous not to exceed this upper temperature limit.

SUMMARY OF THE INVENTION

A process for the preparation of 4-nitrophenetol by reaction of 4-chloronitrobenzene with ethanol and alkali metal hydroxides in the presence of phase-transfer catalysts has now been found, which is characterized in that the reaction is carried out at temperatures from 60° to 95° C. and under pressure in the presence of oxygen-containing gases diluted with inert gases, there being at the start of the reaction 0.2 to 1.0 mol of alkali metal hydroxide metered each hour into the reaction mixture fore each 1 mol of 4-chloronitrobenzene.

DETAILED DESCRIPTION OF THE INVENTION

Phase-transfer catalysts which may be mentioned are the customary quaternary organic ammonium salts, such as tetrabutylammonium bromide, benzyltripropylammonium chloride, benzyldodecyldimethylammonium chloride, benzyltriethylammonium chloride and/or benzyltrimethylammonium chloride. Benzyltrimethylammonium chloride may be mentioned as preferred.

The phase-transfer catalysts are generally used in an amount of about 1 to 5% by weight, preferably 1.5 to 3.5% by weight, relative to the starting material. It is possible in an advantageous manner to prepare the phase-transfer catalysts in the reaction vessel before the start of the actual reaction. Thus, for example, it is possible to prepare benzyltrimethylammonium chloride by reaction of trimethylamine and benzyl chloride in ethanol.

Examples of alkali metal hydroxides suitable for the process according to the invention are sodium and/or potassium hydroxide. The alkali metal hydroxides can be metered into the reaction mixture both in solid form and in aqueous or alcoholic solution. Thus, for example, a 50% strength aqueous solution of sodium hydroxide is preferred. The amount of alkali metal hydroxides is generally about 2 to 5 mol, particularly preferably 2.5 to 4 mol, of alkali metal hydroxide per mol of 4-chloronitrobenzene.

In order to prevent the formation of, especially, 4,4'-dichloroazoxybenzene by reductive dimerization of 4-chloronitrobenzene, care should be taken that the addition of the alkali metal hydroxide, for example, the sodium hydroxide solution, to the reaction mixture does not take place at an arbitrarily fast rate. When the phase-transfer concentrations are small the initial part of the reaction is particularly critical. Thus, in the first 1½ to 2½ hours, preferably in the first 2 hours, only about 0.2 to 1.0 mol of alkali metal hydroxide should be added per mol of starting material and per hour. An amount of 0.3 to 0.6 mol of alkali metal hydroxide per mol of starting material and per hour is preferred. In the subsequent course of the reaction, the amount of alkali metal hydroxide added is no longer critical and can be increased to above 1 mol per hour, so that in about 4 to 6 hours the total amount of alkali metal hydroxide has been metered in.

The maintenance of a low base concentration in the reaction mixture is assisted by efficient stirring of the reaction mixture, especially the phase boundary, even at industrial stirring speeds.

Both air and oxygen are suitable as oxygen-containing gases. In the process according to the invention they are mixed with inert gas, such as nitrogen, for injection into the reaction mixture. The pressure of the oxygen-containing gas used in the process according to the invention is about 1 to 10 bar, preferably 2 to 8 bar. In this context, the pressure of the oxygen-containing gas which is injected in is governed by the ratio of the batch size to the autoclave volume and can readily be determined by preliminary tests. Thus, for example, with a 1 mol batch in a 0.7 l autoclave an initial pressure of 1 to 4 bar, preferably from 1.5 to 3.5 bar, of air is required at 83° C.

The amount of inert gas which is admixed to the oxygen-containing gas can be varied within wide limits. The amount of inert gas added is at least sufficient to prevent the formation of explosive mixtures. This can likewise readily be determined by appropriate tests.

The ethanol can be used in the process according to the invention both in the pure form and, in a preferred manner, as an industrial product with a content of about 95% by weight. About 1.0 to 1.6 mol of ethanol, preferably 1.1 to 1.4 mol of ethanol, is required per mol of starting material.

The reaction temperature is about 60° to 95° C., preferably 75° to 90° C., particularly preferably 80° to 85° C.

The amounts of phase-transfer catalysts required in the process according to the invention are substantially less than in known processes, which means that the process according to the invention takes a particularly economical form. It is then possible to remove the phase-transfer catalyst, in the small concentration remaining, from the waste water in an elegant manner and without industrial problems.

Moreover, the process according to the invention is not sensitive to elevated reaction temperatures. Even at temperatures above 80° C. there is, surprisingly, virtually no formation of azoxy by-products. This means that the working up, purification and further processing of the 4-nitrophenetol is considerably facilitated. The 4-nitrophenetol can be removed in the melt without emulsion formation. In addition, despite the elevated reaction temperature, negligible amounts of 4-nitrophenol are formed, which likewise facilitates the working up of the reaction product.

In contrast to the know processes, the process according to the invention is not carried out in a stream of air but in a closed system. This means that the danger of an explosive zone composed of an ethanol/air mixture in the exit gas stream is avoided. Thus, the process according to the invention contributes to increasing process safety.

The invention will now be described with reference to the following non-limiting examples.

EXAMPLE 1

157.6 g, 1 mol, of 4-chloronitrobenzene, 67.8 g, 1.4 mol, of ethanol (95% pure) and 5.6 g of benzyltrimethylammonium chloride (3 mol-%) were initially introduced at 83° C. into a 1 l autoclave. Compressed air was injected to an internal pressure of 2 bar, and 210 ml of 50% strength aqueous sodium hydroxide solution was pumped in at the following rate: 1st hour: 20 ml, 2nd hour: 30 ml, then 50 ml/h. The internal pressure rose to 2.8 bar. The mixture was then stirred at 83° C. for 6 hours. After the pressure had been released, 220 ml of hot water were added, and the organic phase was separated off and washed twice with 70 ml of hot water. The product crystallized out with a pale yellow color on cooling. The combined aqueous phases were subjected to incipient distillation, and a little product which had precipitated out at room temperature was filtered off with suction. Yield: 165 g, 98.7% of theory, melting point 57°–58° C., purity 99.25%, 0.75% starting material. The product obtained is free of 4,4'-dichloroazoxybenzene and 4-nitrophenol.

The waste water contained 0.1 to 0.2 g of 4-nitrophenol.

EXAMPLE 2

157.6 g of 4-chloronitrobenzene, 67.8 g of ethanol (95% pure) and 4.6 g of benzyltrimethylammonium chloride (2.5 mol-%) were initially introduced at 83° C. into a 0.7 l autoclave. Compressed air was injected to 3.3 bar, and $N_2$ was injected to 6.5 bar internal pressure. Then 160 ml of 50% strength aqueous sodium hydroxide solution were pumped in as follows: 1st hour: 20ml, 2nd hour: 30 ml, 3rd hour: 40 ml, then 50 ml/h. The internal pressure rose to 10 bar. The mixture was stirred at 83° C. for a further 5–6 hours, the pressure was released, and 170 ml of hot water were added. The organic phase was removed and washed twice with 70 ml of water at 70° C. The combined aqueous phases were subjected to incipient distillation and filtered with suction at room temperature. Yield: 165.5 g, 99% of theory, purity 97%. The product was free of azoxy by-products and of 4-nitrophenol.

EXAMPLE 3

1 mol of 4-chloronitrobenzene, 1.2 mol of ethanol (95% pure) and 10 g of benzyltriethylammonium chloride were initially introduced at 83° C. and under a pressure of 7 bar of air into a 0.7 l autoclave. 210 ml of 50% strength aqueous sodium hydroxide solution were pumped in within 4 hours, and the mixture was stirred for a further 8 hours. The pressure rose to 10 bar. Working up was conducted as in Example 1. The product contained 1.2% of starting material, no azoxy by-product and no 4-nitrophenol.

EXAMPLE 4

(Comparison Example)

Example 1 was repeated with the exception that no oxygen-containing gas (air) was injected. After the autoclave had been closed it was heated to 83° C. This resulted in an autogenous pressure of 1 bar. The product obtained after working up still contained 1.2% of starting material and contained 5.6% of 4,4'-dichloroazoxybenzene.

EXAMPLE 5

(Comparison Example)

Example 2 was repeated with the exception that, with 3 mol-% benzyltrimethylammonium chloride, 210 ml of 50% strength sodium hydroxide solution was pumped in within 3 hours. The product contained 0.3% of starting material and 0.2% of 4,4'-dichloroazoxybenzene.

It will be appreciated that the instant specification and examples are set forth by way of illustration and not limitation, and that various modifications and changes may be made without departing from the spirit and scope of the present invention.

What is claimed is:

1. A process for the preparation of 4-nitrophenetol comprising reacting 4-chloronitrobenzene with ethanol and an alkali metal hydroxide in the presence of a phase-transfer catalyst, the reaction being carried out at temperatures from 80° to 95° C. and under pressure in the presence of oxygen-containing gases at an initial pressure of 1 to 4 bars to attain a total pressure of 2 to 10 bars of the oxygen-containing gas which in the process is mixed with inert gases, there being at the start of the reaction 0.2 to 1.0 moles of alkali metal hydroxide metered each hour into the reaction mixture for each 1 mole of 4-chloronitrobenzene, wherein the amount of inert gas admixed to the oxygen-containing gas is at least sufficient to prevent the formation of explosive mixtures.

2. A process according to claim 1, wherein the pressure of the oxygen containing gas is 2 to 8 bars.

3. A process according to claim 1, wherein the oxygen-containing gas is air.

4. A process according to claim 1, wherein the oxygen-containing gas is oxygen.

5. A process according to claim 1, wherein the temperature is 80° to 90° C.

6. A process according to claim 1, wherein the temperature is 80° to 85° C.

7. A process according to claim 1, wherein 0.2 to 1.0 moles of alkali metal hydroxide per 1 mole of 4-chloronitrobenzene per hour are added in the first $1\frac{1}{2}$ to $2\frac{1}{2}$ hours of the reaction.

8. A process according to claim 1, wherein 0.2 to 1.0 moles of alkali metal hydroxide per 1 mole of 4-chloronitrobenzene per hour are added in the first 2 hours of the reaction.

9. A process according to claim 1, wherein 0.3 to 0.6 moles of alkali metal hydroxide are added per hour for each 1 mole of 4-chloronitrobenzene.

10. A process according to claim 1, wherein the inert gas is nitrogen.

11. A process according to claim 1, wherein the phase transfer catalyst is selected from the group consisting of tetrabutylammonium bromide, benzyltripropylammonium chloride, benzyldodecyldimethylammonium chloride, benzyltriethylammonium chloride and benzyltrimethylammonium chloride.

12. A process according to claim 1, wherein the alkali metal hydroxide is contained in an amount of 2 to 5 moles per mole of 4-chloronitrobenzene.

13. A process according to claim 1, wherein the alkali metal hydroxide is contained in an amount of 2.5 to 4 moles per mole of 4-chloronitrobenzene.

14. A process according to claim 1, wherein the alkali metal hydroxide is selected from the group consisting of sodium hydroxide and potassium hydroxide.

* * * * *